(12) United States Patent
Fernandez

(10) Patent No.: US 6,233,342 B1
(45) Date of Patent: May 15, 2001

(54) SUNGLASSES WITH ADJUSTABLE VENTILATION

(75) Inventor: Ernie Fernandez, San Jose, CA (US)

(73) Assignee: Pan-Optx, Inc., Pleasanton, CA (US)

( * ) Notice: Subject to any disclaimer, the term of this patent is extended or adjusted under 35 U.S.C. 154(b) by 0 days.

(21) Appl. No.: 09/608,443

(22) Filed: Jun. 29, 2000

(51) Int. Cl.[7] .................................................. G02C 11/08
(52) U.S. Cl. .................................. 381/62; 2/235; 2/236; 2/237
(58) Field of Search ............................. 351/62, 41, 158; 2/437, 436, 435

(56) References Cited

U.S. PATENT DOCUMENTS

| | | | |
|---|---|---|---|
| D. 339,596 | 9/1993 | Kopfer | D16/102 |
| 1,936,746 | 11/1933 | Baker | 2/14 |
| 1,989,876 | 2/1935 | Meyrowitz | 2/14 |
| 2,002,543 | 5/1935 | Meyrowitz | 2/14 |
| 2,321,159 | 6/1943 | Ryan | 88/41 |
| 2,364,584 | 12/1944 | Malcom | 2/14 |
| 4,707,863 | 11/1987 | McNeal | 2/436 |
| 4,785,481 | 11/1988 | Palmer, III et al. | 2/436 |
| 4,877,320 | 10/1989 | Holden | 351/44 |
| 5,191,364 | 3/1993 | Kopfer | 351/62 |
| 5,428,411 | 6/1995 | Kopfer | 351/62 |
| 5,711,035 | * 1/1998 | Haslbeck | 2/436 |

FOREIGN PATENT DOCUMENTS 364970   1/1931   (GB).

* cited by examiner

*Primary Examiner*—Hung Xuan Dang
(74) *Attorney, Agent, or Firm*—Medlen & Carroll, LLP

(57) ABSTRACT

Eyewear is disclosed for use in sports and the like which allows the wearer to adjust the flow of air across the inside surface of the lens without having to remove the eyewear. The eyewear includes a frame shaped to fit a wearer's face, one or two lenses mounted in the frame, and a temple bracket mounted on each side of the frame. Each temple bracket has a front surface substantially contiguous with the front surface of the frame and containing an inlet opening. An inner surface of each temple bracket contains an outlet opening and a passageway connecting the inlet opening and outlet opening. A block is positioned for sliding movement in the passageway and is connected to a button mounted for sliding movement on the outer surface of each temple bracket. When the end of the block proximal to the inlet opening is moved away from the inlet opening and past the outlet opening, air can flow from the inlet opening, through the passageway and out of the outlet opening, causing a flow of air, drawing air through ventilation openings in the frame. When the end of the block proximal to the inlet opening is moved towards the inlet opening and past the outlet opening, obstructing the outlet opening, the air flow is turned off.

14 Claims, 6 Drawing Sheets

SUNGLASSES WITH ADJUSTABLE VENTILATION

TECHNICAL FIELD OF THE INVENTION

This invention relates generally to eyewear for use in sports and the like; and more particularly to eyewear which is ventilated to reduce or prevent fogging, increase comfort and protect from the wind.

BACKGROUND OF THE INVENTION

Eyewear used for sports is typically designed to wrap around the user's face and sufficiently seal against the skin to create a dead air space between the glasses and the user's face (hereinafter referred to as the "dead space"). As the user engages in strenuous activity, the heat and moisture can build up in the dead space, making the glasses uncomfortable to wear and producing condensation on the inside surface of the lenses which can partially or entirely obstruct the vision of the wearer. This phenomenon is commonly known as "fogging."

There have been many prior art methods attempted to reduce or eliminate fogging. Some devices, such as that described in U.S. Pat. No. 4,707,863, describe chemical coatings which can be applied to the inside surface of a lens to alleviate fogging. Such coatings, however, tend to enhance fingerprints caused by handling, and are typically not durable, tending to wear off when the user cleans the lenses.

Therefore, different types of ventilation have been relied upon to alleviate fogging. Many prior art sunglasses and protective glasses or goggles provide openings in the frame above and below the lenses to allow air to flow in and out. These are not believed to be particularly effective at preventing fogging when a wearer is engaged in particularly strenuous activity, since there is nothing to cause the air to actually flow through the dead space, unless the wearer tilts his head downward towards the ground as he is moving forward to allow the passing air to flow through the perforations in the frame. This is not particularly desirable when the wearer is moving forward at great speed (for example, when riding a motorcycle) because such action will take the wearer's eyes off the space in front of his vehicle and may result in an unfortunate accident. Moreover, when the user can generate a flow through the dead space, there is no way to control the amount of air throughput or turn it off when it is no longer desired. Finally, open apertures will typically allow the ingress of dust and particulate matter into the dead space where it can be blown into the unprotected eyes by the flow of air, which is also very undesirable.

U.S. Pat. Nos. 5,191,364 and 5,428,411 substantially reduced or eliminated the ingress of dust and particulate matter into the dead space by covering the ventilation apertures with permeable foam, and further addressed the fogging problem with coated and/or double lenses. However, these glasses still suffer from the lack of a motivating force for causing a flow of air through the ventilating apertures without causing the wearer to take his eyes off his direction of travel.

British Patent Specification 364,970 addressed the problem of controlling a flow of air through the dead space by providing a valve which may be adjusted by loosening a screw, rotating an inlet regulating disc to a desired position, and then tightening the screw. This device is not desirable because the user must remove the glasses, produce a screw driver, loosen the screw, rotate the disc, tighten the screw, put the glasses back on and use them at the desired speed to determine if the disc has been rotated to a position which will produce the desired flow under the specific conditions of use. If not, the procedure must be repeated over and over again until the desired flow is obtained.

Accordingly, the need exists for sunglasses and protective glasses which automatically generate a flow of filtered air through the dead space which can be easily adjusted by the user while wearing and using the sunglasses, without the need for removing them.

SUMMARY OF THE INVENTION

In one embodiment, the present invention provides eyewear for use in sports and the like having a frame shaped to fit a wearer's face the frame having a lens mounting surface for mounting a lens means for protecting a wearer's eyes, and a temple bracket on each side of the frame, each temple bracket having a front surface substantially contiguous with the front surface of the frame, a rear surface, an inner surface and an outer surface, the temple bracket including an inlet opening on the front surface of the temple bracket, an outlet opening on the inner surface of the temple bracket, a passageway between the inlet and outlet openings for the flow of air, and a block slidable in the passageway to selectively open and close the passageway between the inlet and outlet openings, a control means mounted on the outer surface of said temple bracket to permit the wearer to move the block in the passageway to adjust the flow of air, without the need of removing the eyewear, a lens mounted on the lens mounting surface, and a temple bars or a strap for securing the eyewear on the head of the wearer.

Other and further objects, features, advantages and embodiments of the present invention will become apparent to one skilled in the art from reading the Detailed Description of the Invention together with the drawings.

DETAILED DESCRIPTION OF THE INVENTION

Figure 7:
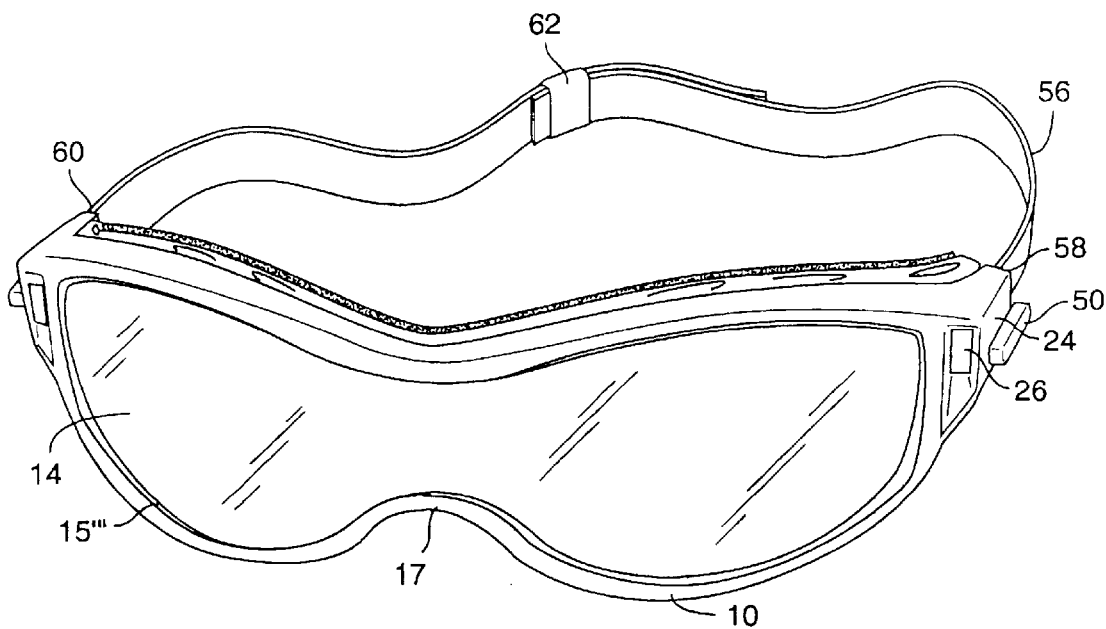
FIG. 7 is a front view of another embodiment of eyewear of the present invention.
Figure 8A:
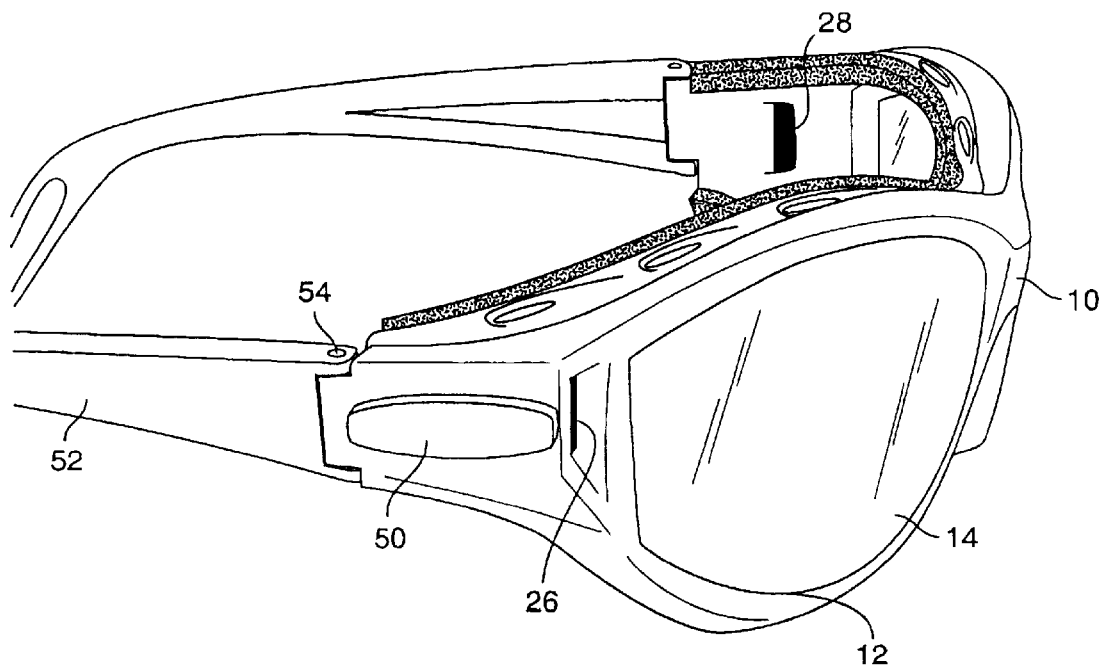
FIGS. 8A and 8B are perspective side views of the eyewear of FIG. 1 showing button 50 in a closed position (8A) and in an open position (8B).
Figure 8B:
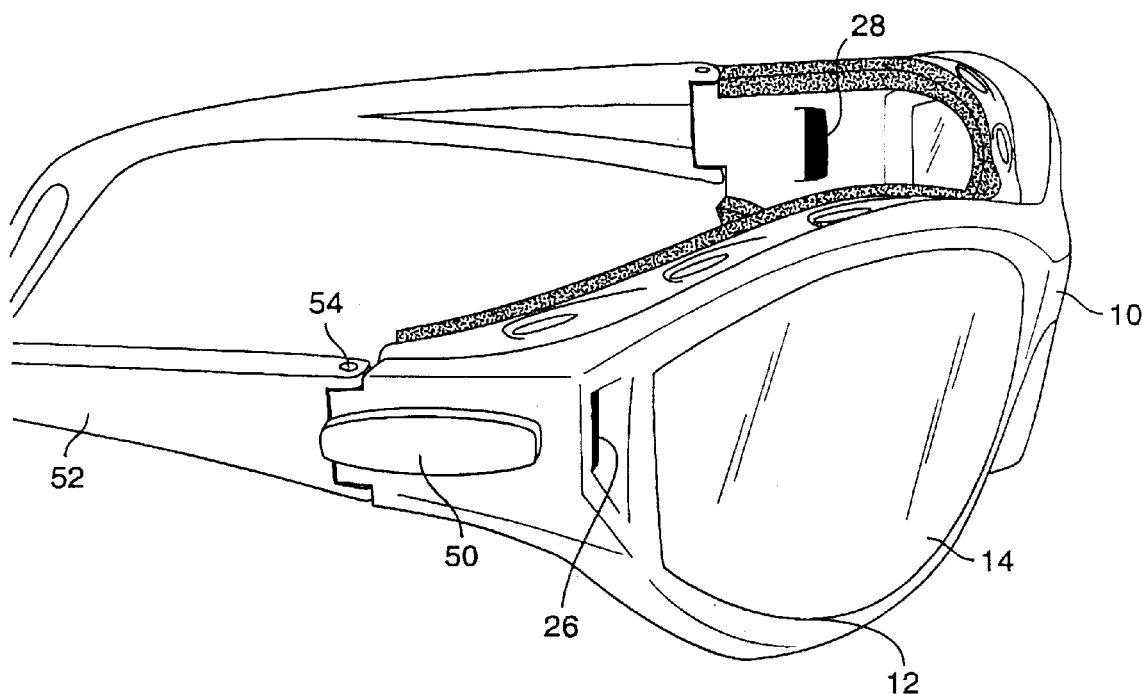

As shown in FIGS. 1–3 and 7, eyewear of the present invention includes a frame 10, which is preferably formed from a resilient material such as plastic. Metal frames, while less desirable, can also be used. The frame 10 includes an aperture for the eyes of the wearer which is circumscribed by a lens mounting surface 12, on which one or more lenses 14 are mounted. Lenses 14 are conventionally mounted to the lens mounting surface, and may be tinted or coated to provide protection against the rays of the sun, and/or may be corrective lenses to correct the vision of far-sighted or near-sighted wearers. Most preferably, the frames 10 are provided with two eye apertures, a right eye aperture 15' aligned with the wearer's right eye and a left eye aperture 15 aligned with the wearer's left eye. However, as shown in FIG. 7, the frame may be constructed to provide a single aperture 15" for both eyes, which is covered with a single lens 14. Frame 10 is most preferably curved to closely fit against the wearer's face.

Frames 10 are also preferably provided with a nose bridge 17 to support the eyewear on the bridge of the user's nose. A pair of temple bars 52, 52', shown in FIGS. 1–3, or an adjustable elastic strap 56, shown in FIG. 7, can be conventionally used to support the frames 10 on the user's head.

Figure 1:
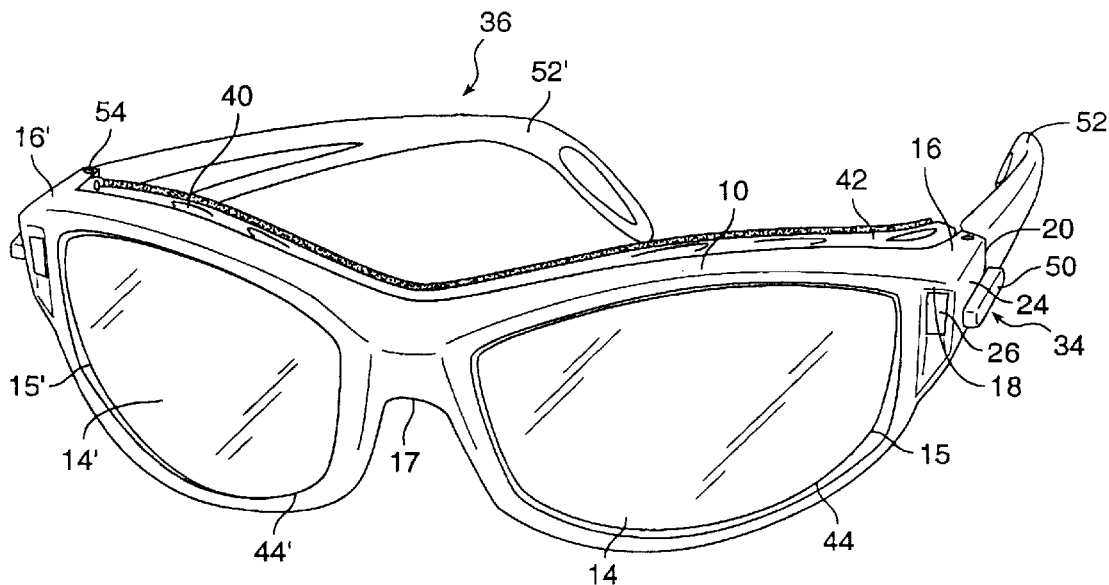
FIG. 1 is a perspective front view of eyewear of the present invention.
Figure 2:
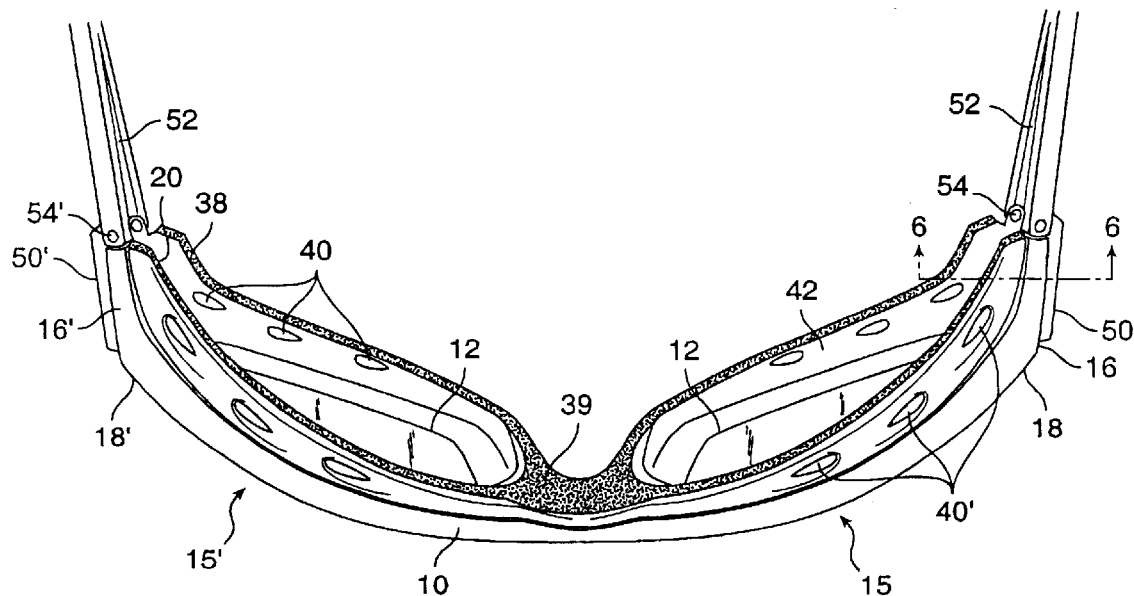
FIG. 2 is a perspective top view of the eyewear of FIG. 1.
Figure 3:
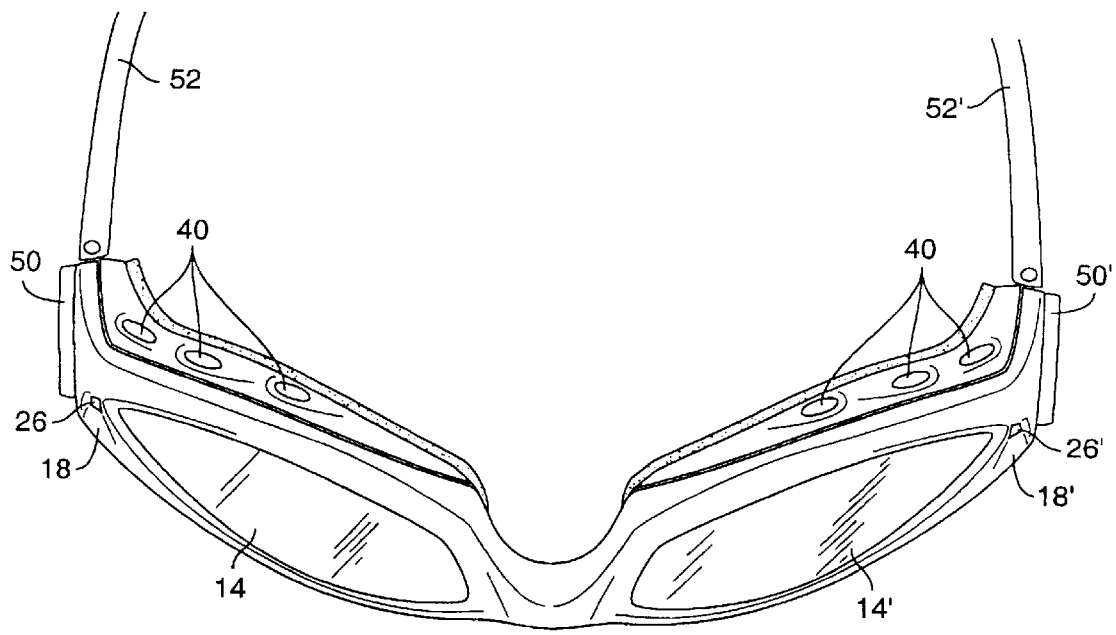
FIG. 3 is a perspective bottom view of the eyewear of FIG. 1.
Figure 4:
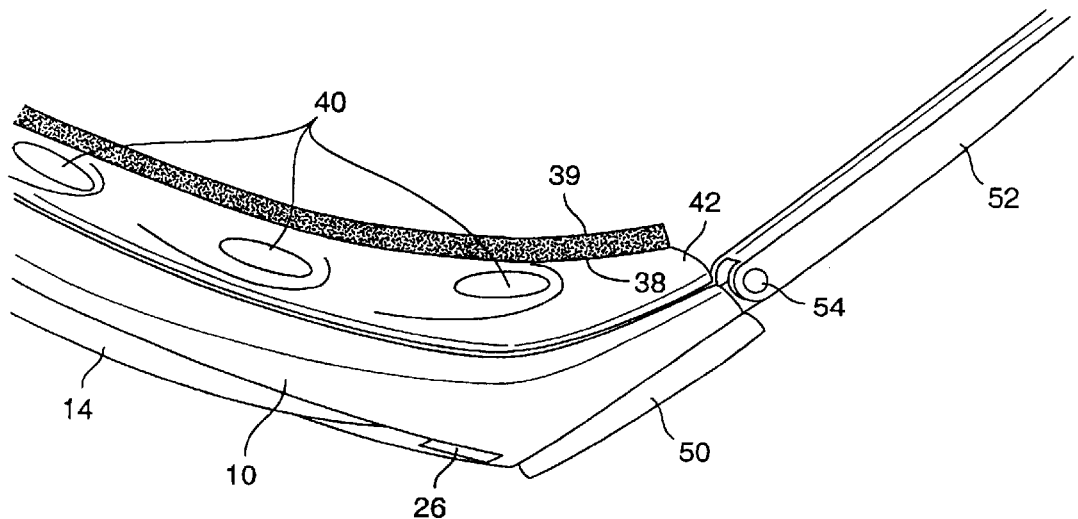
FIG. 4 is a partial view showing the temple bracket of the eyewear of FIG. 1.
Figure 5:
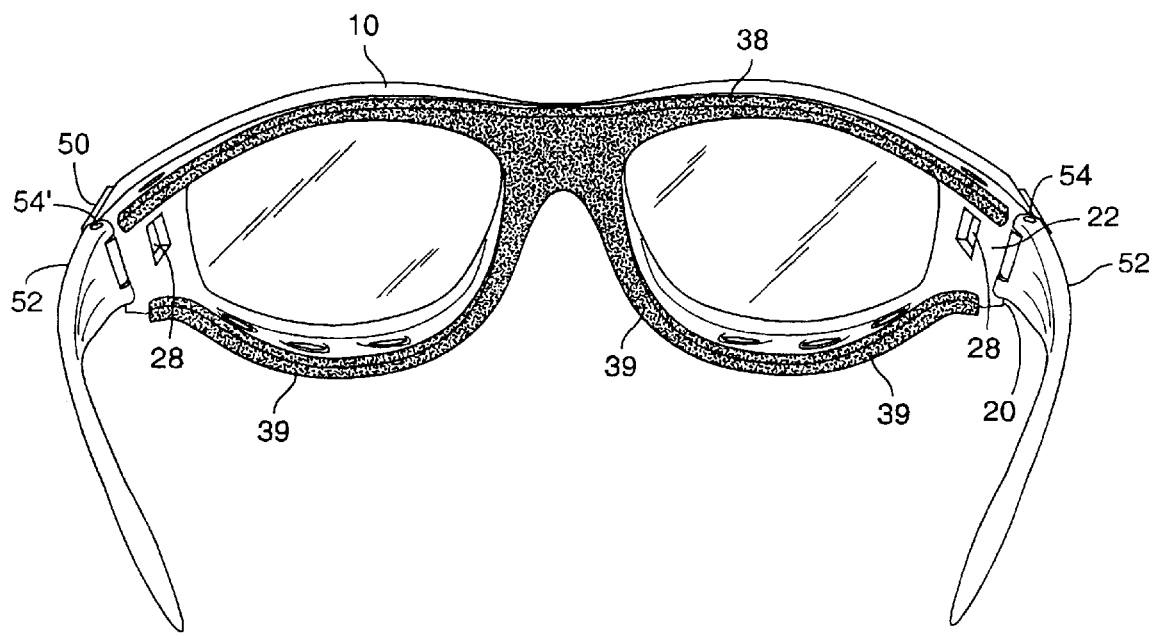
FIG. 5 is a rear view of the eyewear of FIG. 1.
Figure 6A:
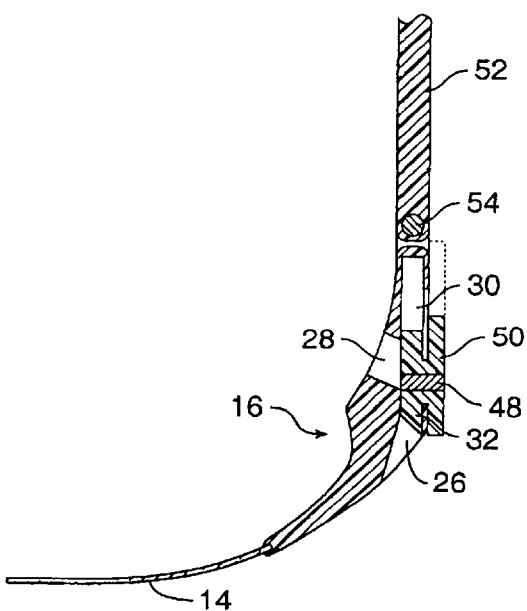
FIGS. 6A–6C are cross-sectional views taken through 6—6 of FIG. 2 in which button 50 is moved from a closed position (6A) to a partially open position (6B) to a fully open position (6C)
Figure 6B:
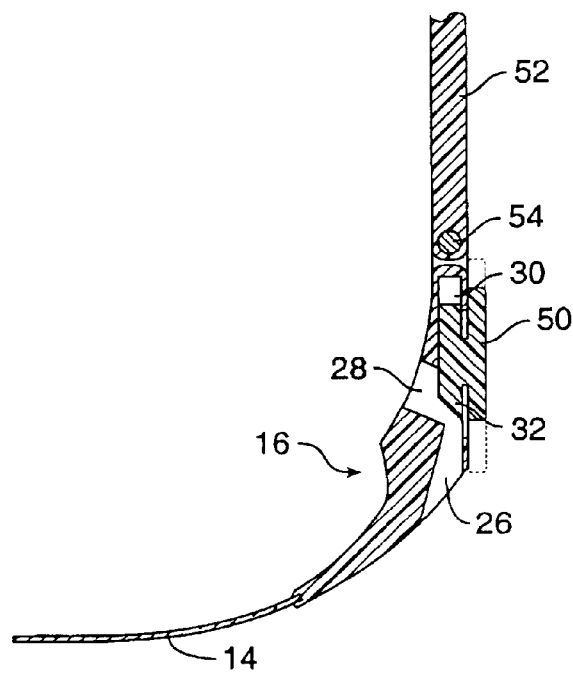
Figure 6C:
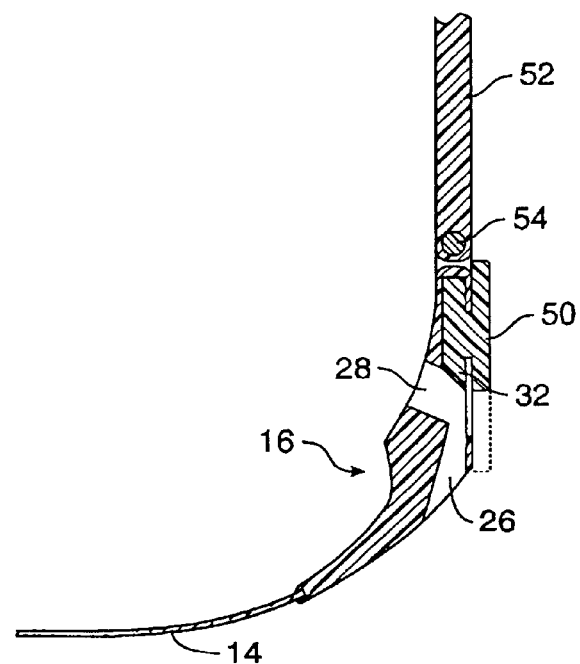

The inside of frame 10 is preferably provided with a spacing means or web 42 contoured to fit a wearer's face closely while spacing the lenses from the wearer's face to create a dead space between the user's eyes and the lenses. Web 42 is preferably provided with ventilation apertures 40, 40' and a sealing surface 38. Ventilation apertures 40, 40' are most preferably covered on their inside surface (e.g., adjacent to the lenses) with permeable foam to prevent the ingress of dust and particulate matter through the apertures 40, 40'. The sealing surface 38 (shown in FIG. 5) is also preferably covered with permeable foam 39 to provide a comfortable, cushioned, air permeable seal around the wearer's face.

The eyewear of the present invention also includes a temple bracket 16, 16' at each end of frame 10. Temple bracket 16, 16' includes a front surface 18, a rear surface 20, an inner surface 22, an outer surface 24, an inlet opening 26 positioned on the front surface 18, and an outlet opening 28 positioned on the inner surface 22. Front surface 18, 18' of temple bracket 16, 16' respectively is substantially contiguous with the front of the frame 10. Rear surface 20, 20' of temple bracket 16, 16' respectively, provides a surface for connecting the temple bars 52, 52' or strap 56 to the frame. Temple bars 52, 52' are preferably connected to the rear surface 20, 20' of temple bracket 16, 16' to allow the bars 52, 52' to pivot around a hinge pin 54, 54' for selectively folding the bars 52, 52' to a closed position towards the inner surface of the frame or to an open position for mounting on the wearer's head in the well-known conventional fashion. Temple bars 52, 52' may be permanently mounted for such pivoting movement, or may be removably mounted using wellknown, bayonet type mounts which allow for removal of the temple bars 52, 52' and replacement by a strap. Likewise, a strap 56 having a first end 58 and a second end 60 may be permanently or removably mounted to the rear surface 20, 20' respectively of temple bracket 16, 16'. The length of strap 56 can be conventionally adjusted using a buckle or other adjustment means 62 to provide a snug fit against the wearer's face.

As shown in more detail in FIGS. 5–8, inlet opening 26 and outlet opening 28 are connected by a passageway 30. When passageway 30 is not obstructed (see, e.g., FIG. 6B and 6C), air can flow from the inlet opening 26 through passageway 30 and out of outlet opening 28, where it will flow alongside the wearer's temples towards the rear of the head. This air flow at the periphery of the dead space will tend to create lower pressure in the dead space which will draw air through the ventilating apertures 40. Because the inlet opening 26 is located on the front surface 18 of temple bracket 16, the wearer does not need to turn his head in a direction which will take his eyes off the direction he is traveling towards in order to create a flow of air across the inside surface of lenses 14.

As the ability to control the flow of air is highly preferred, a sliding block 32 is provided in the passageway 30. To allow the wearer to move the sliding block 32 in the passageway 30, a horizontal slot is preferably provided through the outer surface of the temple bracket to allow a device, such as button 50, to be conventionally mounted to the sliding block 32, for example, by using a pin 48. If the end of block 32 proximal to inlet opening 26 is cut to be perpendicular to the sides of block 32, then block 32 will provide some control over the flow of air, depending primarily on the width of the outlet opening. For example, the air flow through the outlet opening 28 will be cut approximately in half when the block 32 obstructs half the outlet opening 28. More preferably, the end of block 32 is shaped like a wedge to allow for finer control of flow. Once block 32 is moved towards the inlet opening 26 and completely obstructs the outlet opening 28, the air flow through the outlet opening 28 will stop. Device 50 should be easily movable by the wearer while the eyewear is being worn. We prefer to use a button as shown, and use the surface of the button to provide a logo or other identifying information for the eyewear. To prevent the ingress of dust or particulate matter, permeable foam can be mounted inside the inlet opening 26 or the outlet opening 28 or both. We prefer placing permeable foam in the outlet opening 28.

To use eyewear of the present invention, the wearer places the eyewear on his face so that his eyes are aligned with the lens 14, the nose bridge is resting on the nose, the means 36 for mounting the frame on the users face is engaging the user's head, and the sealing area is engaging the user's face. If the user finds a lens 14 is fogging, or otherwise desires to increase the flow of air through the dead space, the user simply slides button 50 in a rearwards direction away from the inlet opening 26 until the desired or maximum flow is obtained. If the user finds the flow of air through the dead space is excessive, the user simply slides button 50 in a forwards direction towards the inlet opening 26 until the desired flow, or no flow, is obtained. In this configuration, the air flow on each side of the eyewear is independently controlled.

One skilled in the art will recognize at once that it would be possible to construct the present invention from a variety of materials and in a variety of different ways. While the preferred embodiments have been described in detail, and shown in the accompanying drawings, it will be evident that various further modification are possible without departing from the scope of the invention as set forth in the appended claims.

What is claimed is:

1. Eyewear for use in sports and the like comprising:
    a frame shaped to fit a wearer's face and having a lens mounting surface for mounting a lens means for protecting a wearer's eyes, and a temple bracket on each side of the frame, said temple bracket having a front surface substantially contiguous with the front surface of the frame, a rear surface, an inner surface and an outer surface, said temple bracket including an inlet opening on the front surface of the temple bracket, an outlet opening on the inner surface of the temple bracket, a passageway between said inlet and outlet openings, and a block slidable in said passageway to selectively open and close the passageway between said inlet and outlet openings;
    a control means mounted on the outer surface of said temple bracket for moving said block in said passageway;
    a lens means mounted on said lens mounting surface a means for mounting the frame to the head of the wearer attached to each temple bracket.

2. The eyewear of claim 1 wherein said frame includes a sealing area on an inner surface for engaging a wearer's skin around the eyes.

3. The eyewear of claim 2 wherein said sealing area comprises permeable foam.

4. The eyewear of claim 1 wherein said frame includes ventilation openings along a top and bottom surface.

5. The eyewear of claim 4 wherein said eyewear additionally includes a web interposed between said frame and the wearer, and wherein said ventilation openings are provided in said web.

6. The eyewear of claim 5 wherein said ventilation openings are covered with permeable foam to prevent the ingress of particulate matter.

7. The eyewear of claim 5 wherein said web and said frame are formed together as a unitary structure.

8. The eyewear of claim 1 wherein the lens mounting surface defines two apertures, one for each eye of a wearer.

9. The eyewear of claim 8 wherein each aperture is covered by a lens.

10. The eyewear of claim 1 wherein said control means is a sliding button mounted for sliding movement along the outer surface of the temple bracket and connected to the block by a pin mounted through a longitudinal slot in said temple bracket, said longitudinal slot defining an opening between said outer surface of said temple bracket and said passageway.

11. The eyewear of claim 1 wherein said outlet opening is covered with permeable foam to prevent the ingress of particulate matter.

12. The eyewear of claim 1 wherein said means for mounting the frame to the head of the wearer comprises a temple bar hingedly mounted to the rear surface of each temple bracket, said temple bar shaped to fit a user's head in a region above and behind a user's ears.

13. The eyewear of claim 12 wherein each said temple bar is removably attached to said temple bracket.

14. The eyewear of claim 1 wherein said means for mounting the frame to the head of the wearer comprises an elastic strap having a first and a second end, said first end removably mounted to said rear surface of one of said temple brackets, and said second end removably mounted to said rear surface of the other of said temple brackets.

* * * * *